United States Patent
Bulkes et al.

(10) Patent No.: US 7,535,296 B2
(45) Date of Patent: May 19, 2009

(54) CLASS-E RADIO FREQUENCY POWER AMPLIFIER WITH FEEDBACK CONTROL

(75) Inventors: Cherik Bulkes, Sussex, WI (US); Stephen Denker, Mequon, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 107 days.

(21) Appl. No.: 11/678,247

(22) Filed: Feb. 23, 2007

(65) Prior Publication Data

US 2007/0210867 A1 Sep. 13, 2007

Related U.S. Application Data

(60) Provisional application No. 60/776,853, filed on Feb. 24, 2006.

(51) Int. Cl.
*H03F 3/38* (2006.01)

(52) U.S. Cl. .......................................... 330/10; 330/251

(58) Field of Classification Search .................. 330/10, 330/251, 207 A, 291, 292, 302, 277
See application file for complete search history.

(56) References Cited

U.S. PATENT DOCUMENTS

| | | | |
|---|---|---|---|
| 5,179,511 A | 1/1993 | Troyk et al. | |
| 5,329,249 A | 7/1994 | Cripps | |
| 6,073,050 A | 6/2000 | Griffith | |
| 6,445,953 B1 | 9/2002 | Bulkes et al. | |
| 6,522,194 B1 * | 2/2003 | Pehlke | 330/10 |
| 6,758,551 B2 | 7/2004 | Tien et al. | |
| 6,864,668 B1 | 3/2005 | McCune et al. | |
| 6,864,755 B2 | 3/2005 | Moore | |
| 6,889,087 B2 | 5/2005 | Moore | |
| 7,005,935 B2 | 2/2006 | Moore | |
| 7,023,267 B2 | 4/2006 | Lee et al. | |
| 7,352,237 B2 * | 4/2008 | Snelgrove et al. | 330/10 |
| 2003/0071731 A1 | 4/2003 | Jesme | |
| 2005/0096702 A1 | 5/2005 | Denker et al. | |
| 2005/0187584 A1 | 8/2005 | Denker et al. | |
| 2006/0217089 A1 | 9/2006 | Snelgrove et al. | |

FOREIGN PATENT DOCUMENTS

WO  WO 01/28629 A1  4/2001

* cited by examiner

*Primary Examiner*—Khanh V Nguyen
(74) *Attorney, Agent, or Firm*—Quarles & Brady; George E. Haas

(57) ABSTRACT

A Class-E power amplifier includes a choke and a switch connected in series between a source of a supply voltage and circuit ground and connected to an inductively coupled coil. An output node of the amplifier is formed between choke and the switch and connected to a transmitter antenna. A shunt capacitor couples the amplifier's output node to the circuit ground. A feedback signal, indicating an intensity if the signal at the amplifier output node is used to vary the input signal to the Class-E power amplifier and thereby control operation of the switch.

10 Claims, 2 Drawing Sheets

CLASS-E RADIO FREQUENCY POWER AMPLIFIER WITH FEEDBACK CONTROL

CROSS-REFERENCE TO RELATED APPLICATIONS

This application claims benefit of U.S. Provisional Patent Application No. 60/776,853 filed Feb. 24, 2006.

STATEMENT REGARDING FEDERALLY SPONSORED RESEARCH OR DEVELOPMENT

Not Applicable

BACKGROUND OF THE INVENTION

1. Field of the Invention

The present invention relates to radio frequency power amplifiers, and more particularly to a radio frequency Class-E power amplifier with feedback control.

2. Description of the Related Art

A remedy for a patient with a physiological ailment is to implant an electrical stimulation device that provides provide therapy to the patient. An electrical stimulation device is a small electronic apparatus that stimulates an organ or part of an organ with electrical pulses. It includes a pulse generator, implanted in the patient, and from which electrical leads extend to electrodes placed adjacent to specific regions of the organ.

An improved apparatus for physiological stimulation of a tissue includes a wireless radio frequency (RF) receiver implanted as part of a transvascular platform that comprises at least one stent-electrode that is connected to the wireless RF receiver and an electronic capsule containing a stimulation circuitry. The stimulation circuitry receives the radio frequency signal and, from the energy of that signal, derives an electrical voltage for powering the implanted device. The electrical voltage is applied in the form of suitable waveforms to the electrodes, thereby stimulating the tissue of the organ.

The radio frequency (RF) signal generation is a significant part of the electrical stimulation apparatus and it usually involves the use of an RF amplifier. The RF amplifier of choice typically has been a Class-A or Class-AB amplifier in those cases where linearity is of utmost concern. The class of an analog amplifier defines what proportion of the input signal cycle is used to actually switch on the amplifying device. A Class-A amplifier is switched on 100% of the time. A Class-AB amplifier uses a signal cycle that is greater than 50%, but less than 100% to switch on the amplifying device. Unfortunately, these amplifiers are not very efficient and dissipate a significant amount of energy. The efficiency of a power amplifier is defined as the ratio of output power and input power expressed as a percentage.

Recently, a different kind of amplifier, known as a switching amplifier, has been developed. A particularly useful switching amplifier is called a Class-E amplifier. Switching amplifiers have relatively high power efficiency due to the fact that perfect switching operation does not dissipate power. An ideal switch has zero impedance when closed and infinite impedance when open, implying that there is zero voltage across the switch when it conducts current (on state) and zero a non-zero voltage across it in the non-conductive state (off state). Consequently, the product of voltage and current (power loss) is zero at any time. Therefore, a Class-E amplifier has a theoretical efficiency of 100%, assuming ideal switching.

From a theoretical standpoint, a Class-E amplifier can provide very efficient RF amplification. However, in practice, Class-E amplifiers do not achieve anywhere close to the theoretical limits. Some embodiments of the prior art techniques use a relaxation oscillator to drive the amplifier. With this technique, it is impossible to control the range of the power depending on the need. In other embodiments, a regulator is used to control the power feed. In this case, heat is generated in the control system itself and the amplifier's efficiency is subsequently lowered. Therefore, there is a need to improve the performance of practical Class-E RF power amplifiers based on the fundamental understanding of the loss generation processes. An optimal design can make the heat dissipation so low such that heat-sink is not required.

SUMMARY OF THE INVENTION

The present invention provides a Class-E radio frequency power amplifier with feedback control.

A Class-E power amplifier includes a switch; a choke connected in series with the switch between a source of a supply voltage and circuit ground. An amplifier output node is formed between choke and the switch and is connected to a load. A shunt capacitor couples the amplifier output node to the circuit ground. An output sensor produces a feedback signal indicating an intensity of a signal applied to the load and the feedback signal is employed to vary the radio frequency input signal.

In a preferred embodiment, the switch comprises a semiconductor device, such as a MOSFET. Ideally the semiconductor device has a feedback capacitance that is less than 10% of its input capacitance. It also is preferred that channel resistance and a peak current rating of the semiconductor device are such that the arithmetic product of the channel resistance and the peak current rating is less than 3% of the supply voltage.

DETAILED DESCRIPTION OF THE INVENTION

Although the present Class-E power amplifier with feedback control is described with respect to an intravascular implanted device, it should be understood that the power amplifier is applicable for a number of medical and non-medical applications. Such other applications include, but are not limited to, medical imaging power amplifiers, such as are used for MRI radio frequency power amplification, implants (e.g. intravascular amplifiers, cochlear), high voltage amplifiers and in general, wherever a highly efficient, practical signal power amplification is required with a feedback control.

Figure 1:
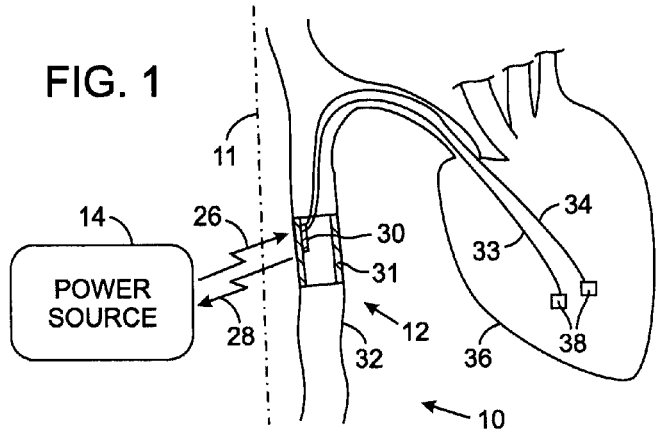
FIG. 1 is a schematic diagram of a wireless transvascular platform, that includes external and internal components, for stimulating tissue inside a patient.

With initial reference to FIG. 1, a wireless transvascular platform 10 for tissue stimulation includes an extracorporeal power source 14 and a medical device 12 implanted inside the body 11 of an animal. The extracorporeal power source 14 includes a battery that powers a transmitter that sends a first radio frequency (RF) signal 26 to the medical device 12. The medical device 12 derives electrical power from the energy of the first radio frequency signal 26 uses that power to energize and electronic circuit 30 mounted on an electronic carrier 31. The first radio frequency signal 26 also carries commands to configure the operation of the medical device.

A second RF signal 28 enables the medical device 12 to transmit operational data back to the extracorporeal power source 14. Such data may include physiological conditions of the animal, status of the medical device and trending logs, for example, which have been collected by the implanted electronic circuit 30 and sent via the second radio frequency signal 28. This data is provided transmitted by the extracorporeal power source 14 monitoring equipment so that medical personnel can review the data or be alerted when a particular condition exists.

The implanted medical device 12 includes the electronic circuit 30 mentioned above which has an RF transceiver and a tissue stimulation circuit, similar to that used in conventional pacemakers and defibrillators. That electronic circuit 30 is located in a large blood vessel 32, such as the inferior vena cava (IVC), for example. One or more, electrical leads 33 and 34 extend from the electronic circuit 30 through the animal's blood vasculature to locations in the heart 36 where pacing and sensing are desired. Each lead has an electrical conductor enclosed in an electrically insulating outer layer. The electrical leads 33 and 34 terminate at electrode assemblies 38 at those locations.

Figure 2:
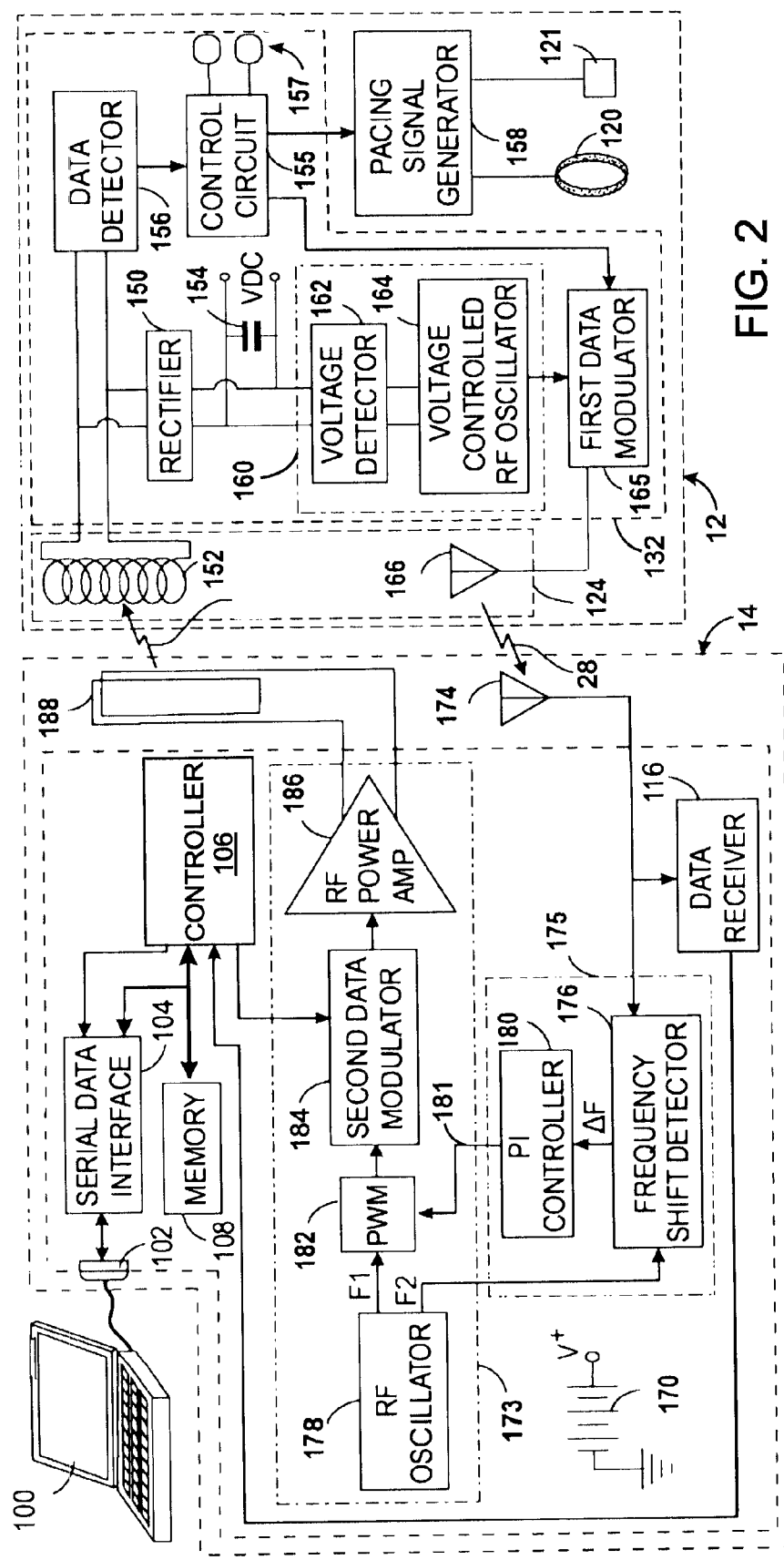
FIG. 2 is a schematic diagram of an exemplary implanted medical device with an external component containing a Class-E RF amplifier.

With reference to FIG. 2, the internal components comprise an implanted medical device 12 includes a stimulation circuit 132 having a first receive antenna 152 within the antenna assembly 124 in which the antenna is tuned to pick-up a first RF signal 26 at a first radio frequency F1. The first receive antenna 152 is coupled to a data detector 156 that recovers data and commands carried by the first RF signal 26. That data specifies operational parameters of the medical device 12, such as the duration that a stimulation pulse is applied to the electrodes 120 and 121. The recovered data is sent to a control circuit 155 for that medical device, which stores the operational parameters for use in controlling operation of a pacing signal generator 158 that applies tissue stimulating voltage pulses across the electrodes 120 and 121.

The control circuit 155 also is connected to a pair of sensor electrodes 157 that detect electrical activity of the heart and provide conventional electrocardiogram signals which are utilized to determine when cardiac pacing should occur. Additional sensors for other physiological characteristics, such as temperature, blood pressure or blood flow, may be provided and connected to the control circuit 155. The control circuit stores a histogram of pacing, data related to usage of the medical device, and other information which can be communicated to the extracorporeal power source 14 or another form of a data gathering device that is external to the patient.

The first receive antenna 152 also is connected to a rectifier 150 that extracts energy from the received first RF signal. That energy is used to charge a storage capacitor 154 that supplies electrical power to the components of the implanted medical device 12. Specifically, the radio frequency, first RF signal 26 is rectified to produce a DC voltage (VDC) that is applied across the storage capacitor 154.

The DC voltage produced by the rectifier 150 also is applied to a feedback signal generator 160 comprising a voltage detector 162 and a voltage controlled, first radio frequency oscillator 164. The voltage detector 162 senses and compares the DC voltage to a nominal voltage level desired for powering the medical device 12. The result of that comparison is a control voltage that indicates the relationship of the actual DC voltage derived from the received first RF signal 26 and the nominal voltage level. The control voltage is fed to the control input of the voltage controlled, first radio frequency oscillator 164 which produces an output signal at a radio frequency that varies as a function of the control voltage. For example, the first radio frequency oscillator 164 has a center, or second frequency F2 from which the actual output frequency varies in proportion to the polarity and magnitude of the control signal and thus deviation of the actual DC voltage from the nominal voltage. For example, the first radio frequency oscillator 164 has a first frequency of 100 MHz and varies 100 kHz per volt of the control voltage with the polarity of the control voltage determining whether the oscillator frequency decreases or increases from the second frequency F2. For this exemplary oscillator, if the nominal voltage level is five volts and the output of the rectifier 150 is four volts, or one volt less than nominal, the output of the voltage controlled, first radio frequency oscillator 164 is 99.900 MHz (100 MHz-100 kHz). That output is applied to via a first data modulator 165 to a first transmit antenna 166 of the implanted medical device 12, which thereby emits a second RF signal 28. Data regarding physiological conditions of the animal and the status of the medical device 15 are sent from the control circuit 155 to the first data modulator 165 which amplitude modulates the second RF signal 28 with that data.

As noted previously, the electrical energy for powering the medical device 12 is derived from the first RF signal sent by the extracorporeal power source 14. The extracorporeal power source 14 uses power from a rechargeable battery 170 to periodically transmit pulses of the first RF signal 26. The first RF signal 26 is pulse width modulated to vary the magnitude of energy received by the implanted medical device 12. The pulse width modulation is manipulated to control the amount of energy the medical device receives to ensure that it is sufficiently powered without wasting energy from the battery 170 in the extracorporeal power source 14. Alternatively, the first RF signal 26 can also be modulated by amplitude modulation to vary the magnitude of energy received by the implanted medical device 12.

To control the energy of the first RF signal 26, the extracorporeal power source 14 contains a second receive antenna 174 that picks up the second RF signal 28 from the implanted medical device 12. Amplitude modulated data is extracted from the second RF signal 28 by a data receiver 116 and sent to the controller 106. Because the second RF signal 28 also indicates the level of energy received by medical device 12, this enables extracorporeal power source 14 to determine whether medical device should receive more or less energy. The second RF signal 28 is sent from the second receive antenna 174 to a feedback controller 175 which comprises a frequency shift detector 176 and a proportional-integral (PI) controller 180. The second RF signal 28 is applied to the frequency shift detector 176 which also receives a reference signal at the second frequency F2 from a second radio frequency oscillator 178. The frequency shift detector 176 compares the frequency of the received second RF signal 28 to the second frequency F2 and produces a deviation signal ΔF indicating a direction and an amount, if any, that the frequency of the second RF signal has been shifted from the second frequency F2. As described previously, the voltage controlled, first radio frequency oscillator 164, in the medical device 12, shifts the frequency of the second RF signal 28 by an amount that indicates the voltage from rectifier 150 and thus the level of energy derived from the first RF signal 26 for powering the implanted medical device 12.

The deviation signal ΔF is applied to the input of the proportional-integral controller 180 which applies a transfer function given by the expression $GAIN/(1+s_i\tau)$, where the GAIN is a time independent constant gain factor of the feedback loop, $\tau$ is a time coefficient in the LaPlace domain, and $s_i$ is the LaPlace term containing the external frequency applied to the system. The output of the proportional-integral controller 180 on line 181 is an error signal indicating an amount that the voltage (VDC) derived by the implanted medical device 12 from the first RF signal 26 deviates from the nominal voltage level. That error signal corresponds to an arithmetic difference between a setpoint frequency and the product of a time independent constant gain factor, and the time integral of the deviation signal.

The error signal is sent to the control input of a pulse width modulator (PWM) 182 which forms an amplitude modulator within a power transmitter 173 and produces at output signal that is on-off modulated as directed by the error input. The output from the pulse width modulator 182 is fed to a second data modulator 184 which modulates the signal with data from the controller 106 for the medical device 15. The second data modulator 184 feeds the RF signal to a Class-E type RF power amplifier 186 from which the signal is applied to a second transmit antenna 188.

In addition to transmitting electrical energy to the implanted medical device 15, the extracorporeal power source 14 transmits operational parameters which configure the functionality of the medical device. The implanted medical device 15 also sends operational data to the extracorporeal power supply. A data input device, such as a personal computer 100, enables a physician or other medical personnel to specify operating parameters for the implanted medical device 15. Such operating parameters may define the duration of each stimulation pulse, an interval between atrial and ventricular pacing, and thresholds for initiating pacing. The data defining those operating parameters are transferred to the extracorporeal power source 14 via a connector 102 connected to the input of a serial data interface 104. The data received by the serial data interface 104 can be applied to a microprocessor based controller 106 or stored directly in a memory 108.

Figure 3:
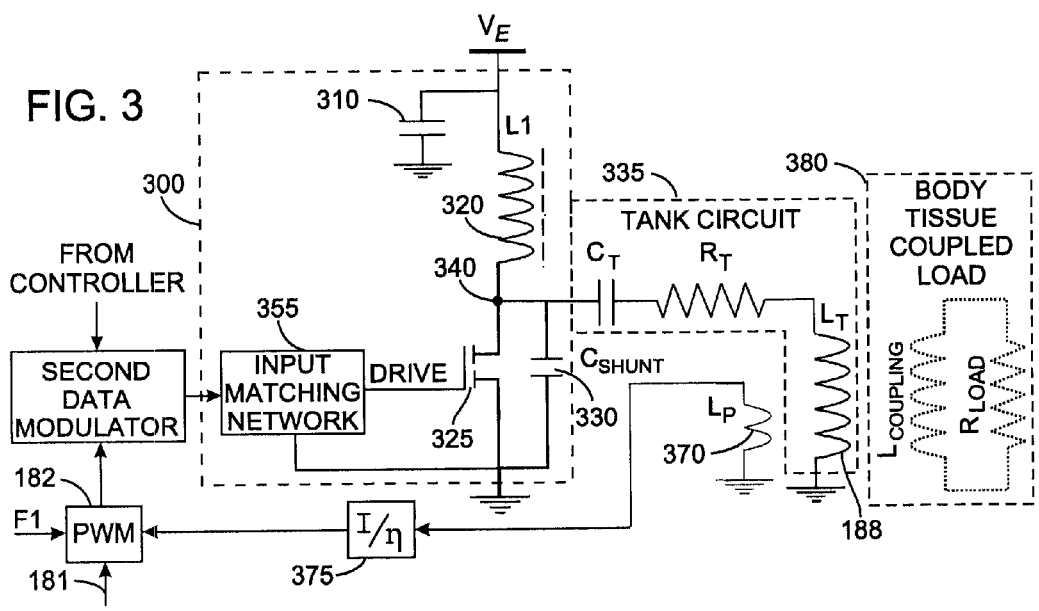
FIG. 3 is a detailed schematic diagram of the Class-E RF amplifier.

FIG. 3 illustrates a unique Class-E amplifier 300 that is employed as the RF power amplifier 186. The modifications comprise an overrated switch with low channel resistance and feedback capacitance, a drive circuit closely integrated with the switch, a mechanism to tune components by adjusting the drive frequency, and an oscillator the duty cycle of which is controlled by non-linearly manipulating a sinusoidal drive signal.

Figure 4:
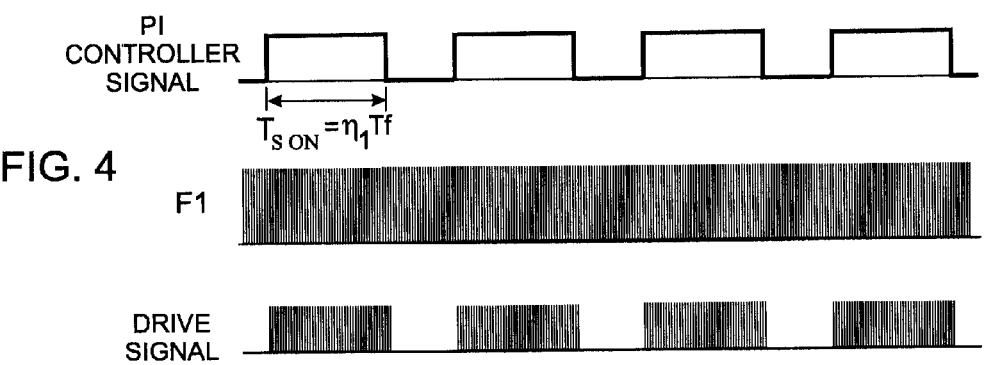
FIG. 4 depicts waveforms for signals in the Class-E RF amplifier.

The Class-E amplifier 300 is operated by a voltage or current of the output signal from the second data modulator 184, which is passed through an input matching network 355 in which the mixed modulator signal is AC coupled to a fraction of the sine wave signal and the base line is shifted by a suitable design parameter. The waveform of the drive signal at the output of the second data modulator 184 is depicted in FIG. 4. The drive signal is formed by pulses of the first radio frequency F1 that are present during the on time of the amplifier 300 wherein the pulse duty cycle is determined by the signal on line 181 from the proportional-integral controller 180. The period that the amplifier is on is given by $Ts_{ON}=\eta_1 Tf$, where Tf is the total time of on and off periods that form one signal cycle, and $\eta_1$ is the ratio of on time and the total time. Note that Tf=1/F1. These higher frequency pulses provide finer control of the drive signal without affecting the first radio frequency F1, as occurred with prior methods. Note that this unique pulse design also makes the design more robust and relatively immune to load variations. Thus it allows tuning of components by slight adjustment of drive frequency and control of the output power of the amplifier.

The Class-E RF power amplifier 300 has a supply input connected to a source of a supply voltage $V_E$ and coupled to ground by an input capacitor 310. A choke 320 couples the supply voltage $V_E$ to the switch 325. The choke 320 maintains the current that flows through the switch 325 during its on time, such that after the switch opens, the current flow is distributed between a shunt capacitor 330 and a resonant tank circuit 335, that includes the second transmit antenna 188. The ratio of this distribution is a function of the phase of the periodic cycle of the resonant tank circuit 335 and of the timings of the switch 325. For maximum efficiency, the switch 325 should close while the voltage across the shunt capacitor 330 is substantially to zero.

The switch 325 is a low impedance device, preferably a MOSFET. It is important to over specify the switch 325 by preferably an order of magnitude or more. For example, if the maximum expected current is one ampere, the switch should be rated to handle a transient current of up to ten amperes. The switch element has a low channel resistance and low feedback capacitance. The channel resistance preferably should be such that the arithmetic product of channel resistance and the peak current rating of the switch is less than 3% of the supply voltage $V_E$ to the amplifier 300. The feedback capacitance preferably should be such that it is less than 10% of the input circuit capacitance. The drive circuit 350 is closely integrated with the switch 325 wherein the circuit board layout is chosen based on the selected component configuration, for example by mounting the components as close together as possible. In addition, the loop containing the peak current is spatially located in close proximity to the switch 325.

The tank circuit 335 couples an amplifier output node 340, that is located between the choke 320 and the switch 325, to ground. The tank circuit 335 approximates the resonant waveform that is measurable in an inductively coupled load, as is represented by the "body tissue coupled load" 380. The majority of the coupling with the body tissue is inductive $L_{COUPLING}$ and losses associated with that coupling are represented by $R_{LOAD}$.

To maintain the oscillatory condition, it is desirable to have either predictable phase and gain parameters or control over these parameters. When a load is presented, the drive is increased to meet a predefined setpoint, or a variable setpoint, alternatively a combination of these two methods. In one implementation, it is sufficient to provide a start condition that initially closes the switch 325 for a limited period of time, followed by providing feedback such that the switch is turned off when sufficient current is detected through the tank circuit.

In addition to the power level feedback provided by the implanted medical device 12, it is also possible to provide further feedback control by sampling the output power level at the second transmit antenna 188. One technique for controlling the energy of the first radio frequency signal 26 uses a lower frequency pulse width modulation method. Here, the average output power is sampled and the amplifier is pulse width modulated at a frequency that is one or more orders of magnitude lower than the first radio frequency F1. In one example, the PWM frequency could be 200 kHz for a 20 MHz Class-E amplifier.

In this feedback version, the drive circuit 350 varies the on-time (or duty cycle) of the switch 325 in response to the output of the power transmitter 173 as measured by a pickup coil 370 coupled to the second transmit antenna 188. The voltage induced across the pickup coil 370 is rectified and filtered by an RC network 375 to provide a feedback voltage that is translated by the pulse width modulator 182 to a duty cycle of the drive signal, wherein a greater feedback voltage translates to a lower duty cycle, and a lesser feedback voltage translates to a higher duty cycle. Thus the duty cycle is proportional to the measurement from the pickup coil 370.

The feedback circuit measures the field level generated under load and proportions the drive (on-duration of the amplifier switch 325) accordingly to maintain the oscillatory condition. The feedback circuit may not be self starting. However, it could be operated as a modified self oscillating circuit, in which there is a first radio frequency F1 operated at a minimum idle current. A unique feature of the present invention is the use of a sinusoidal envelope voltage that is non-linearly manipulated to derive the rectangular pulses. This enables the number of components in the Class-E amplifier to be reduced substantially.

For linear applications, the PWM frequency must be selected in conformity with the maximum bandwidth and phase linearity desired in the filtered output signal. For example, the maximum frequency components must be at least one half of the PWM frequency, but may need to be lower depending on the maximum allowed phase variance, which is caused by the digitization process.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. For example, the present invention was described in the context of a device for cardiac stimulation, but can be employed with other types of implanted medical device systems. Accordingly, the scope of the invention should be determined from the following claims and not limited by the above disclosure.

What is claimed is:

1. A Class-E radio frequency power amplifier system that receives a radio frequency input signal and that drives a load, said Class-E radio frequency power amplifier comprising:
    a switch;
    a choke connected in series with the switch between a source of a supply voltage and circuit ground, with an amplifier output node being formed between choke and the switch and connected to the load;
    a shunt capacitor coupling the amplifier output node to the circuit ground;
    an output sensor which produces a feedback signal indicating an intensity of a signal applied to the load; and
    a pulse width modulator that produces an output signal having pulses of the radio frequency input signal wherein the pulses have a duty cycle that varies in response to the feedback signal, and wherein the output signal controls operation of the switch.

2. The Class-E radio frequency power amplifier system as recited in claim 1 wherein the switch is selected from a group consisting of a semiconductor device and a MOSFET.

3. The Class-E radio frequency power amplifier system as recited in claim 1 wherein the switch is a semiconductor device and the feedback signal is proportional to an induced voltage at the load.

4. The Class-E radio frequency power amplifier system as recited in claim 1 wherein the switch is a MOSFET that has a channel resistance and a peak current rating, wherein an arithmetic product of the channel resistance and the peak current rating is less than 3% of the supply voltage applied to the Class-E amplifier.

5. The Class-E radio frequency power amplifier system as recited in claim 1 wherein the switch is rated to conduct a transient current level that is at least ten times a maximum level of a current that the switch is expected to conduct.

6. The Class-E radio frequency power amplifier system as recited in claim 1 wherein the radio frequency input signal has an envelope defined by a control signal.

7. The Class-E radio frequency power amplifier system as recited in claim 1 wherein the amplifier is a component of an MRI scanner.

8. The Class-E radio frequency power amplifier system as recited in claim 1 wherein the amplifier supplies energy to a device implanted in an animal.

9. The Class-E radio frequency power amplifier system as recited in claim 1 wherein the amplifier enables modulated data transmission with power amplification.

10. The Class-E radio frequency power amplifier system as recited in claim 1 wherein the amplifier responds to rectangular pulses derived from non-linear manipulation of a sinusoidal envelope voltage.

* * * * *